United States Patent
Podsędkowski et al.

(10) Patent No.: US 10,624,711 B2
(45) Date of Patent: Apr. 21, 2020

(54) DEVICE FOR MEASURING FEMUR DISPLACEMENT AND METHOD OF MAKING ORTHOPEDIC MEASUREMENTS DURING A SURGICAL PROCEDURE TO CORRECT A DAMAGED HIP

(71) Applicant: POLITECHNIKA ŁÓDZKA, Łódź (PL)

(72) Inventors: Leszek Podsędkowski, Łódź (PL); Michal Panasiuk, Łódź (PL); Agnieszka Kobierska, Łódź (PL); Adam Niewola, Łódź (PL); Mateusz Szaniewski, Łódź (PL)

(73) Assignee: POLITECHNIKA LÓDZKA, Lodz (PL)

( * ) Notice: Subject to any disclaimer, the term of this patent is extended or adjusted under 35 U.S.C. 154(b) by 138 days.

(21) Appl. No.: 15/552,484

(22) PCT Filed: Feb. 23, 2016

(86) PCT No.: PCT/PL2016/000019
§ 371 (c)(1),
(2) Date: Aug. 21, 2017

(87) PCT Pub. No.: WO2016/137347
PCT Pub. Date: Sep. 1, 2016

(65) Prior Publication Data
US 2018/0036093 A1 Feb. 8, 2018

(30) Foreign Application Priority Data
Feb. 24, 2015 (PL) ...................... P.411389

(51) Int. Cl.
*A61B 90/00* (2016.01)
*A61B 5/11* (2006.01)
(Continued)

(52) U.S. Cl.
CPC ............ *A61B 90/06* (2016.02); *A61B 5/1127* (2013.01); *A61B 5/4528* (2013.01);
(Continued)

(58) Field of Classification Search
CPC . A61B 90/06; A61B 2090/065; A61B 5/1127; A61B 5/4528; A61B 5/4571;
(Continued)

(56) References Cited

U.S. PATENT DOCUMENTS

| 5,122,145 A | 6/1992 | Fishbane |
|---|---|---|
| 7,001,346 B2 | 2/2006 | White |

(Continued)

FOREIGN PATENT DOCUMENTS

| WO | 94/12109 A1 | 6/1994 |
|---|---|---|
| WO | 2006/109983 A1 | 10/2006 |

(Continued)

OTHER PUBLICATIONS

Jun. 16, 2016 Search Report issued in International Patent Application No. PCT/PL2016/000019.

(Continued)

*Primary Examiner* — Matthew J Lawson
(74) *Attorney, Agent, or Firm* — Oliff PLC

(57) ABSTRACT

A device for measuring femur bone displacement during total hip arthroplasty includes a base element immovably mounted to the pelvis and a measurement arm, detachably mounted to the base element via a support, and the measurement arm is fitted with a microprocessor computing system with a display screen. The measurement arm includes at least two movable links, serially connected with each other and with support by rotary joints with at least one (and preferably three) degrees of freedom, whereby both movable links are fitted with an accelerometer (preferably a three-axis accelerometer) and/or a magnetic field sensor and/or a gyroscope, preferably forming together an integrated acceleration, magnetic field and gyroscopic sensor unit.

11 Claims, 4 Drawing Sheets

Figure 1:
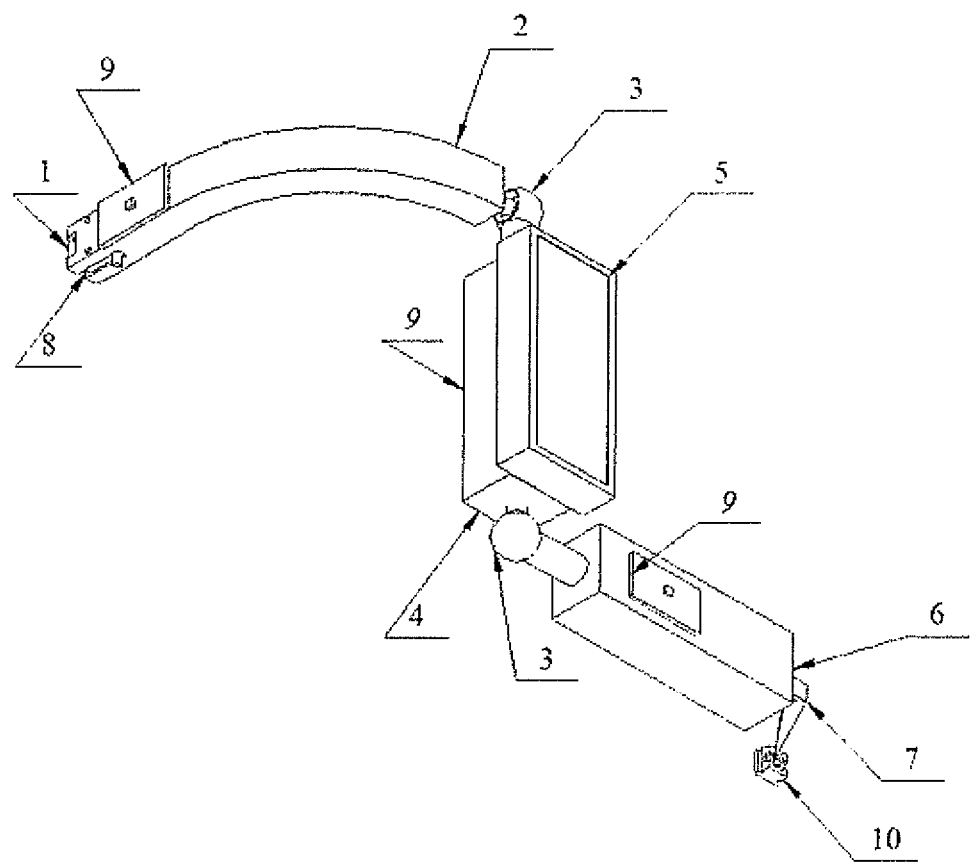

(51) Int. Cl.
*A61F 2/46* (2006.01)
*A61B 17/16* (2006.01)
*A61B 5/00* (2006.01)
*A61F 2/30* (2006.01)

(52) U.S. Cl.
CPC .......... *A61B 5/4571* (2013.01); *A61B 5/6878* (2013.01); *A61B 17/1666* (2013.01); *A61F 2/4657* (2013.01); *A61B 5/1121* (2013.01); *A61B 5/4851* (2013.01); *A61B 2090/061* (2016.02); *A61B 2090/067* (2016.02); *A61B 2505/05* (2013.01); *A61B 2562/0219* (2013.01); *A61B 2562/0223* (2013.01); *A61F 2002/30471* (2013.01); *A61F 2002/469* (2013.01); *A61F 2002/4658* (2013.01); *A61F 2002/4668* (2013.01)

(58) Field of Classification Search
CPC ............... A61B 17/1166; A61B 7/1164; A61F 2090/067; A61F 2/4657
USPC .................................................. 606/300–321
See application file for complete search history.

(56) References Cited

U.S. PATENT DOCUMENTS

| | | | | |
|---|---|---|---|---|
| 10,265,193 | B2* | 4/2019 | Sherman | A61F 2/4609 |
| 10,363,149 | B2* | 7/2019 | van der Walt | A61F 2/4657 |
| 10,413,428 | B2* | 9/2019 | Duval | A61B 5/1079 |
| 2004/0254584 | A1 | 12/2004 | Sarin et al. | |
| 2005/0203540 | A1* | 9/2005 | Broyles | A61B 17/1742 606/102 |
| 2006/0264969 | A1 | 11/2006 | Leitner et al. | |
| 2009/0076519 | A1 | 3/2009 | Iversen | |
| 2011/0208093 | A1* | 8/2011 | Gross | A61B 5/4528 600/587 |
| 2012/0143268 | A1* | 6/2012 | Burroughs | A61B 34/20 606/86 R |
| 2012/0190971 | A1* | 7/2012 | de Wekker | A61B 90/39 600/424 |
| 2014/0052149 | A1* | 2/2014 | van der Walt | A61F 2/4657 606/130 |
| 2014/0094925 | A1* | 4/2014 | Satterthwaite | A61B 17/58 623/22.12 |
| 2014/0275940 | A1 | 9/2014 | Hladio et al. | |
| 2015/0142372 | A1* | 5/2015 | Singh | A61B 5/4851 702/150 |
| 2017/0151031 | A1* | 6/2017 | Tsusaka | A61B 17/56 |
| 2018/0000447 | A1* | 1/2018 | Stindel | A61B 8/0875 |

FOREIGN PATENT DOCUMENTS

WO 2008/118524 A2 10/2008
WO 2010/011978 A1 1/2010

OTHER PUBLICATIONS

Jun. 16, 2016 Written Opinion issued in International Patent Application No. PCT/PL2016/000019.

* cited by examiner

DEVICE FOR MEASURING FEMUR DISPLACEMENT AND METHOD OF MAKING ORTHOPEDIC MEASUREMENTS DURING A SURGICAL PROCEDURE TO CORRECT A DAMAGED HIP

This invention relates to device for measuring femur displacement and method of making orthopedic measurements during a surgical procedure to correct a damaged hip, especially during a total hip arthroplasty, enabling the surgeon performing the surgery to verify translation and offset of the femur.

STATE OF ART

From the state of the art are known apparatuses and systems assisting the work of surgeons during total hip arthroplasty.

Polish patent specification No. P.391327 teaches a system for hip arthroplasty surgeries and a system for measuring extremity length changes and offset in hip arthroplasty on the operating table, fitted with devices required for the surgery. The system is characterized in that it contains a device for intraoperative measurement of extremity length changes and offset (UDSOP) using the equal shadow phenomenon, whereby shadow is cast on a measurement table (TP); the said device is fitted with a measuring set located near the operating table (O) and consisting of a source of light (Z) illuminating the projected measured element and the measurement table (TP) of the projected measured element. The method of measuring extremity length changes and offset in hip arthroplasty relies on the shadow projected on the measurement table by the measuring system consisting of the measurement table (TP), a powerful source of focused unidirectional light (Z) illuminating the projected measured element, the projected measured element placed in a fixed position on the proximal part of the femur at the beginning of the surgery, before femoral head dislocation and after repositioning of test elements of the implant; importantly, in the measurement position the extremity is in the same position during each measurement, the table height and the patient's position (lying on his/her side) is fixed; subsequently a drill or a mill is used to make a recess in the operated hip to provide a permanent support for the spike in the cortical bone of the greater trochanter (in its uppermost part), following which the spike is placed in the recess and the apparatus is positioned correctly, and the first point is marked on the measurement table by means of a marker.

In its turn, the international application No. WO2006109983 entitled "Navigation system for hip replacement surgery having reference mechanism and method using the same" teaches a navigation system for an acetabular cup which guides an insertion orientation of the acetabular cup inserted into a pelvis during a total hip replacement surgery, which includes: a pelvis position tracer which includes probes in contact with three particular points of the pelvis placed on an anterior pelvic plane and a first reference mechanism disposed to indicate a specific reference plane when the probes come in contact with the particular points; and a pelvis position indicator which is fixed to the pelvis, and includes a second reference mechanism that is adjustable to indicate a plane parallel to the specific reference plane indicated by the first reference mechanism, or to indicate a plane perpendicular thereto, or to indicate the both planes. Accordingly, an insertion orientation of an acetabular cup can be guided by using a reference mechanism having a simple structure, and the acetabular cup can be accurately guided regardless of changes in the patient's pelvic position during surgery, because a plane used in the insertion of the acetabular cup can be indicated continuously.

The patent publication No. US 2004/0254584 A1 teaches an invention including: a locating system; a computer, interfaced to the locating system and interpreting the positions of tracked objects in a generic computer model of a patient's hip geometry; a software module, executable on the computer, which defines the patient's pelvic plane without reference to previously obtained radiological data, by locating at least three pelvic landmarks; and a pelvic tracking marker, fixed to the pelvic bone and tracked by the locating system, to track in real time the orientation of the defined pelvic plane. Preferably, the system also includes a femoral tracking marker, securely attachable to a femur of the patient and tracked by the locating system to detect changes in leg length and femoral offset.

Another patent publication No. U.S. Pat. No. 7,001,346 B1 teaches a device using electromagnetic field telemetry sensors cooperating with an electromagnetic field generator, allowing for determining position and orientation. The device does not contain a measurement arm and the elements used therein are too expensive for single use.

Patent publications Nos. US 2011/0208093 A1 and WO 2010/011978 teach a solution using gyroscopic sensors and accelerometers that together form an inertial measurement unit for determining anatomical features of the knee during a knee procedure. The device includes an inertial sensor mounted on the femur and a reference sensor device, which allows for measuring only the spatial orientation of the knee flexion axis and the orientation of surgical cutting planes, but it does not compute linear coordinates of these planes and axes.

Patent publication No. US 2014/0052149 A1 teaches a device for measuring hip position and femur position relative to the hip, using gyroscopic sensors that together form an inertial measurement unit. The device is fitted with two such inertial measurement units: one immovably and detachably connected to the pelvis and another coupled with a landmark acquisition probe used for indicating various anatomical points of the patient. The probe is mounted to the base by means of a joint with two rotational degrees of freedom and one translational degree of freedom. The device does not have an additional link between the base and the probe that would be fitted with an inertial measurement unit; probe location measurement is made by means of a scale with a translational displacement measurement system. Such a solution causes a significant increase of the device's dimensions and costs.

Furthermore, the Patent publication No. WO 2008/118524 A2 discloses a device for measuring femur bone displacement during a surgical procedure, including a base element immovably mountable to the pelvis and a measurement arm, detachably mounted to the base element via a support. The measurement arm includes at least two movable links, connected serially to each other and support by means of rotational joints. The movable links are connected with a computing system unit. In the said case the location of the device portions is detected by encoders in the rotational joints, however the intraoperative verification of translation and offset of the femur is not totally possible.

The purpose of the invention is to develop a device facilitating intraoperative verification of translation and offset of the femur, while such device must not reduce the operating field or interfere with the surgeon's work.

NATURE OF THE INVENTION

The herein described invention substantially constitutes a measurement arm consisting of at least two movable links (bodies, segments) connected serially with each other and with an immovable support by means of rotary joints with at least one and preferably three degrees of freedom, whereby both movable links are fitted with an accelerometer (preferably a three-axis accelerometer) and/or a magnetic field sensor and/or a gyroscope, preferably forming an integrated acceleration, magnetic field and gyroscopic sensor.

Preferably, the measurement arm support is connected with the first movable link by means of a Cardan joint or a spherical joint, and the first movable link is connected to the second movable link by means of revolute, Cardan or spherical joints, and the first movable link is fitted with a microprocessor system with a display screen.

Preferably, the device is fitted with a marker mounted to the femur by means of a screw connection.

Furthermore, it is preferable if the second movable link is fitted with an indicator showing the position of characteristic points of the patient's pelvis or the marker.

Optionally, it is preferable if the measurement arm features a movable end link connected to another movable link by means of a spherical or Cardan joint and detachably connected to a marker.

It is also preferable if the movable end link is fitted with an accelerometer and/or a magnetic field sensor and/or a gyroscope.

It is also preferable if the accelerometer, the magnetic field sensor and the gyroscope form together a single sensor unit.

Furthermore, it is preferable if the microprocessor computing system mounted on the support or one of the links of the measurement arm is fitted with a display screen.

It is also preferable if the second movable link is connected to the first movable link by means of a revolute joint.

In another embodiment, the device has a two-piece support consisting of a lower and an upper support, both connected by means of a joint fitted with a motion locking mechanism.

Preferably, accelerometers (with not more than three axes) are mounted on the upper support and on the three links.

In another embodiment, the support is serially connected to at least five movable links and a movable end link by means of revolute joints with one degree of freedom, whereby a three-axis accelerometer is mounted on at least every other link, preferably on all links, and the device is fitted with a microprocessor computing system with a display screen and control buttons, preferably mounted on the measurement arm.

It is also preferable if the device is fitted with a marker mounted to the femur by means of a screw connection, whereby a movable end link is connected to the marker by means of a quickly detachable connection.

It is furthermore preferable if the device has a two-piece support consisting of a lower and an upper support, both connected by means of a joint fitted with a motion locking mechanism.

It is furthermore preferable if revolute joints constitute local narrowings of the material, where elastic deflections take place.

The method of making orthopedic measurements included in the invention is characterized in that across the entire range of movement of the measurement arm the angle of all revolute joints' axes to the vertical remains greater than 30°, and preferably greater than 60°.

Preferably, the microprocessor computing system is used to determine (based on the reading of the gravitation vector direction from accelerometers located on adjacent links of the measurement arm) the angular position of the revolute joint located between said links and subsequently to determine (based on angular positions of revolute joints) the position of the movable end link relative to the upper support, whereby the measurement is made at least twice, and the operating surgeon—using the display screen 5 and buttons—controls such measurement and reads the data indicating the difference between the first and the last position in directions of relevance to the patient.

It is also preferable if the measurement includes reading of data from the sensors over a certain period of time, during which the patient and the device can be immovable or can be moved by the operating team.

The purpose of the herein described invention is to enable intraoperative assessment of the leg length change and offset change relative to original values, without significantly extending the time of the procedure, changing the typical routine of the procedure (due to the presence of large elements mounted to the bone), or requiring mounting of additional elements to the bone beyond the typical operative wound. The above objective is achieved by using a small, sterile, integrated system for assessing spatial position which fully fits a typical operative wound. The system is mounted to small elements screwed to the bone (a base and a marker) by means of a detachable connection and is present only during actual measurement. The base and the marker are mounted to the pelvis and the femur via the existing typical operative wound. Owing to their dimensions, their presence does not obstruct the surgeon's freedom. The device is installed before joint dislocation and records input data. Subsequently it is uncoupled from the base and the marker, and the surgical procedure proceeds as usual. After the acetabular cup, steam and the test neck and head are positioned, the surgeon once again installs the device and assesses offset and length changes. If the results are not satisfactory, he/she removes the device from the marker mounted to the femur, replaces e.g. the head and makes a reassessment after installing the device again. The surgeon keeps changing replaceable elements of the prosthesis until he/she achieves the desired result. These activities do not significantly extend the procedure's duration because they should be performed at all times. However, a subjective clinical assessment carried out by the surgeon on the basis of palpation of knees, ankles and by detection of the play in the acetabular cup is replaced with an objective measurement. Owing to the device's small dimensions there is no risk of operative field contamination or bone damage (fracture, piercing, etc.) caused by the presence of the device. As a result, no additional equipment in the operating theatre is necessary, which means that operating conditions are safer in terms of cleanliness.

BRIEF DESCRIPTION OF THE DRAWINGS AND EXAMPLES

Figure 2:
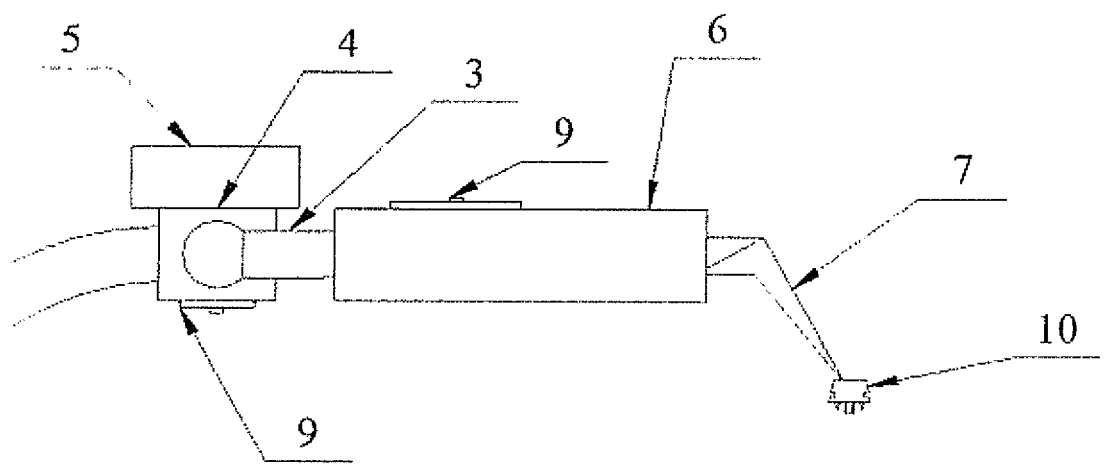
Figure 3:
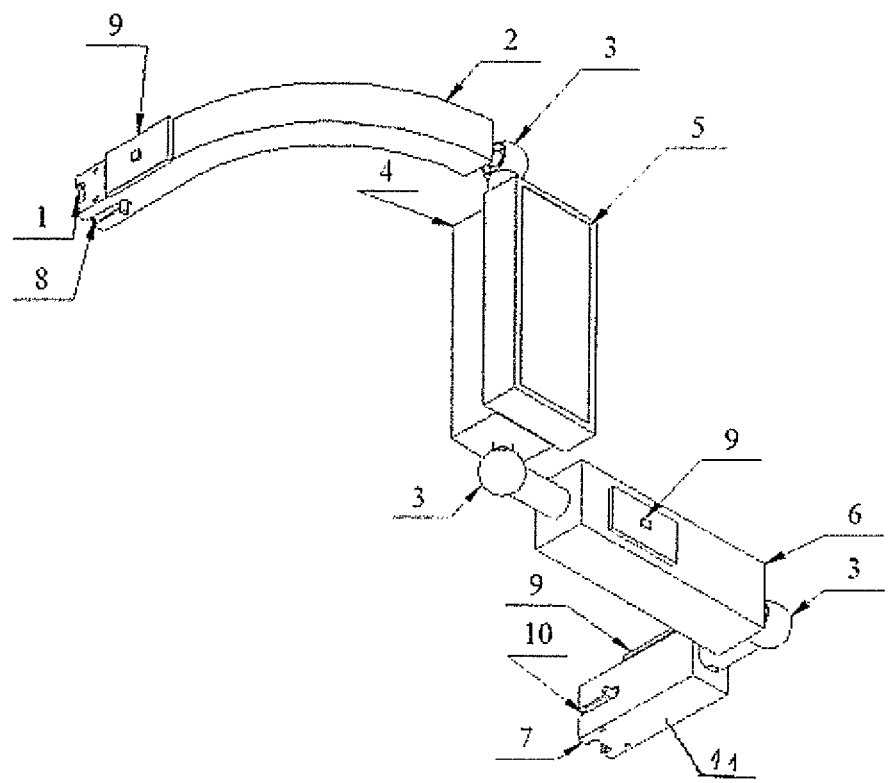
Figure 4:
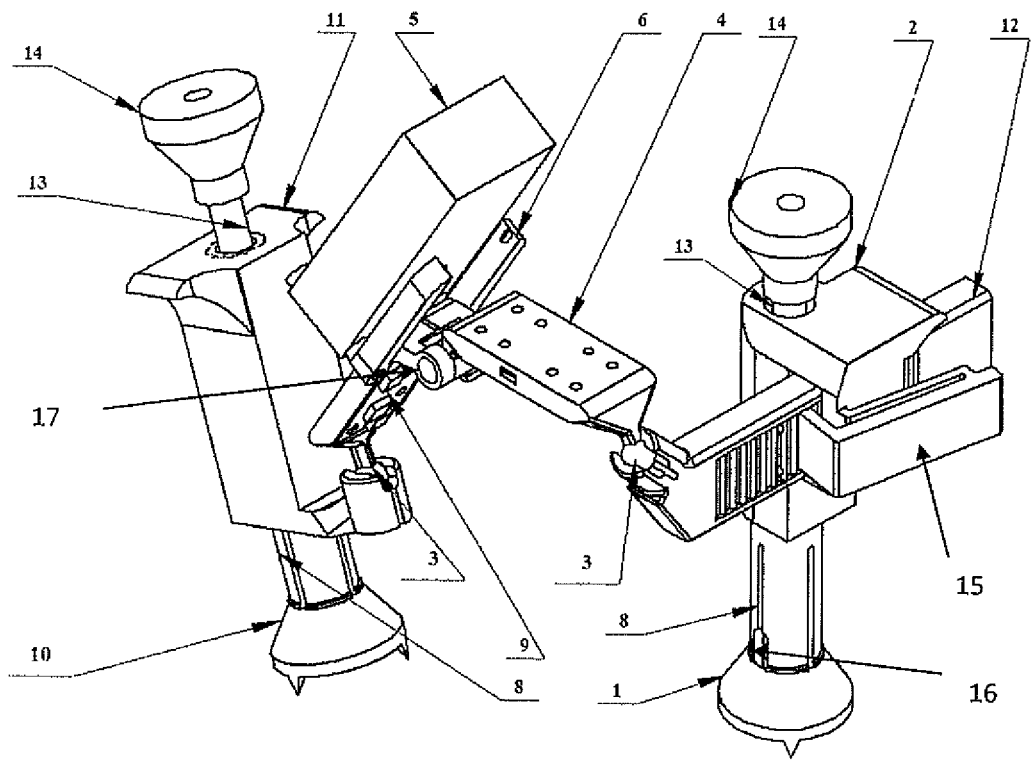
Figure 5:
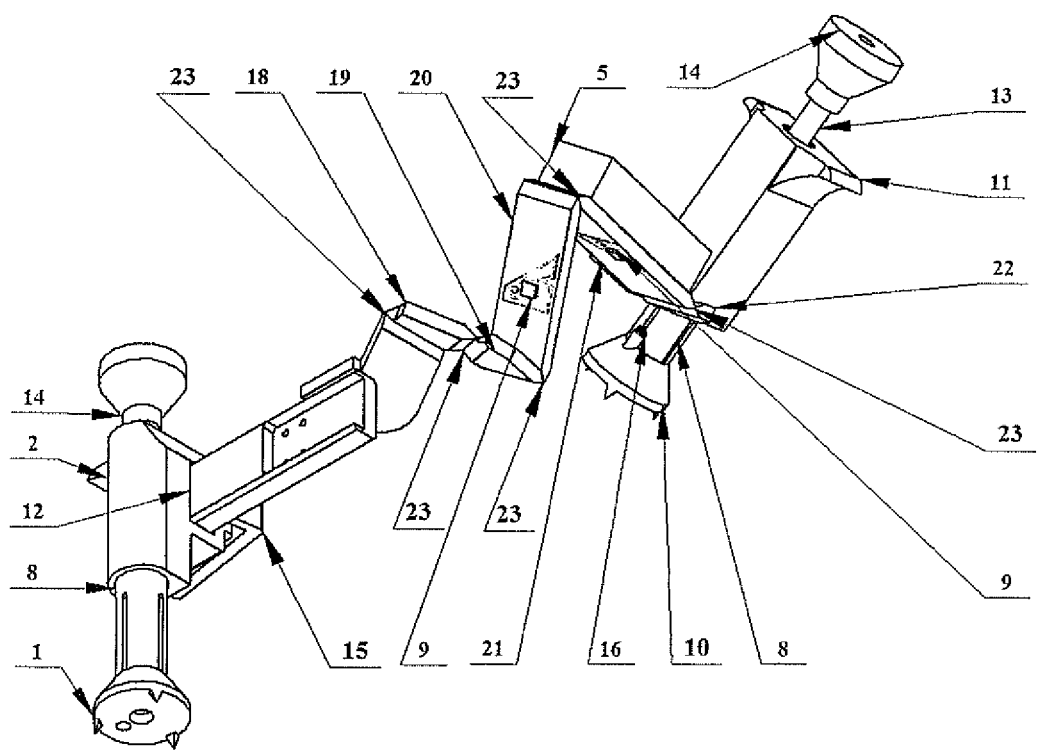
Figure 6:
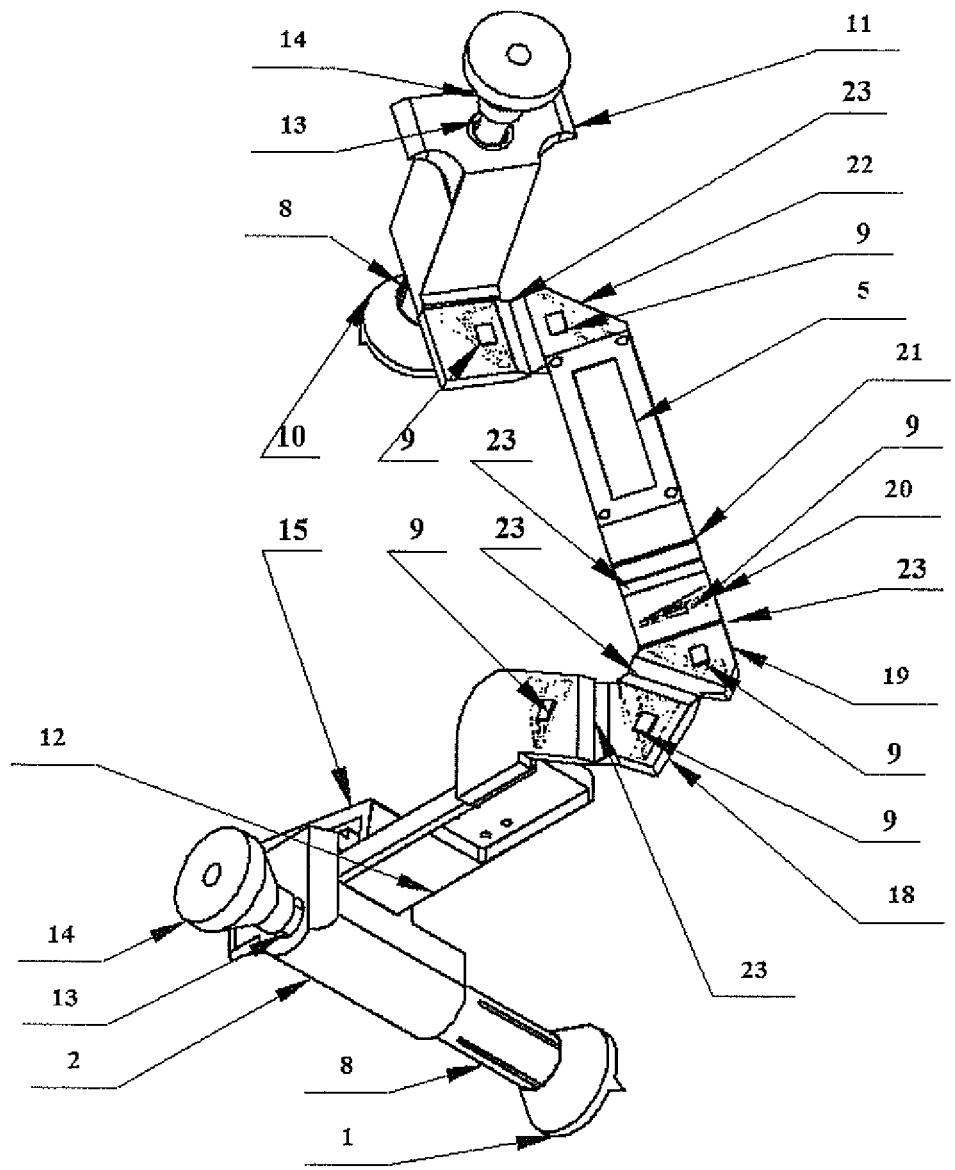

For a more complete understanding of the invention, reference should be made to the embodiments presented on the drawing, wherein:

FIG. 1—measurement arm (perspective view) with two movable links,

FIG. 2—view of the bottom horizontal plane of a detail of the arm from FIG. 1, FIG. 3—measurement arm (perspective view) with three movable links, FIG. 4—measurement arm (perspective view) with three movable links and a two-piece support, fitted with one three-axis accelerometer on each link and one on the upper part of the support, FIG. 5—measurement arm (side perspective view) with six movable links and a two-piece support, fitted with seven three-axis accelerometers, one on each link and one on the upper part of the support, FIG. 6—top perspective view of the measurement arm shown in FIG. 6.

EXAMPLE I—(FIGS. 1 AND 2)

The device for measuring femur bone displacement during total hip arthroplasty includes base element 1 mounted to the pelvis by means of a screw in a manner preventing it from dislocation during the surgical procedure, marker 10 whose displacement relative to the pelvis is measured and which is mounted to the femur by means of a screw connection and measurement arm, detachably mounted to base element 1. The measurement arm includes support 2 mounted to base element 1, movable link I-4 and movable link II-6 with indicator 7. Links 4 and 6 are connected to each other and to the support by means of spherical joint 3. Acceleration sensors, magnetic field sensors and gyroscopic sensors together forming an integrated sensor unit 9 are located on support 2 and on each link 4 and 6. Microprocessor computing system with a display screen 5 and control buttons is mounted on link 4. Its purpose is to compute data provided by sensors and to communicate with the operator (surgeon).

During the surgical procedure and prior to femoral head dislocation, the surgeon mounts the base to the pelvis and the marker to the femur. Subsequently he/she mounts the measurement arm support to the base and brings the tip of link II to the marker. After pushing a button, the measurement system memorizes the differences between angular positions of each link and the support. In this way, the surgeon determines the marker's position relative to the support, and thus to the base and the pelvis. Subsequently the surgeon removes the measurement arm support from the base and proceeds to replace the hip joint. After replacing the femoral head and the acetabular cup, he/she once again mounts the measurement arm to the base and measures the marker's position in the system immovably connected with the base. Subsequently the surgeon sets link II of the measurement arm in the direction in which he/she wishes to measure displacement (translation, offset) and after pressing the corresponding button the system displays a view of the positional difference (before and after hip replacement) in the selected direction.

EXAMPLE II—(FIG. 3)

The device for measuring femur bone displacement during total hip arthroplasty includes base element 1 mounted to the pelvis by means of a screw in a manner preventing it from dislocation during the surgical procedure, marker 10 whose displacement relative to the pelvis is measured and which is mounted to the femur, preferably by means of a screw connection and measurement arm, detachably mounted to base element 1. The measurement arm includes a support mounted to the base element, movable link I-4, movable link II-6 and movable end link III-11 mounted to the marker 10. The form of the marker corresponds to the form of the base element. The links are connected to each other and to the support by means of spherical joints 3. Acceleration sensors, magnetic field sensors and gyroscopic sensors together forming an integrated sensor unit 9 are located on the support and on each link. Microprocessor computing system with a display screen 5 and control buttons is mounted on link I-4. Its purpose is to compute data provided by sensors and to communicate with the operator (surgeon).

EXAMPLE III—(FIG. 4)

The device includes: base element 1, lower section of support 2, upper section of support 12, measurement arm link 4, measurement arm link 6 with microprocessor computing system located on it with a display screen 5 and control buttons, movable end link 11, marker 10, as well as four three-axis accelerometers 9 mounted on links 12, 4, 6, 10, respectively.

Both base 1 and marker 10 take the form of a hollow truncated cone with three sharp spikes protruding downwards and are mounted to the bone by means of a centrally located screw. The measurement arm support includes both lower support 2 and upper support 12 which can linearly move relative to each other after releasing securing lever 15. Lower support 2 is connected with base 1 by means of quickly detachable connection 8 taking the form of an incised sleeve with swellings at the end, inserted into a corresponding socket in base element 1. Rotation of the sleeve relative to base element 1 is blocked by pin 16. After inserting sleeve 8 into base 1 the sleeve is protected against sliding out by pushing rod 13 fitted with handle 14 into it. Link 4 of the measurement arm is connected with upper support 12 by means of spherical joint 3, link 6 of the measurement arm is connected with link 4 of the measurement arm by means of revolute joint 17, movable end link 11 is connected with link 6 by means of spherical joint 3. Furthermore, movable end link 11 is connected with marker 10 by means of quickly detachable connection 8, fitted with locking pin 16 and securing rod 13 with handle 14, identically to the connection of lower section of support 2 with base element 1.

The optional device presented in FIG. 4—owing to the division of the support into two elements—allows for positioning these two elements relative to each other in the first phase of the procedure so as to better adjust the device's position to the patient's anatomy.

EXAMPLE IV—(FIGS. 5 AND 6)

The device includes: base element 1, lower support 2, upper support 12, movable links 18, 19, 20, 21, 22 of a measurement arm, microprocessor computing system with a display screen 5 and control buttons, movable end link 11, marker 10, as well as seven three-axis accelerometers 9 mounted on links 12, 18, 19, 20, 21, 22, 10, respectively. Both base element 1 and marker 10 take the form of a hollow truncated cone with three sharp spikes protruding downwards and are mounted to the bone by means of a centrally located screw. The measurement arm two-piece support includes both lower support 2 and upper support 12 which can linearly move relative to each other after pressing securing lever 15. Lower support 2 is connected with base 1 by means of quickly detachable connection 8 taking the form of an incised sleeve with swellings at the end, inserted into a corresponding socket in base element 1. Rotation of the sleeve relative to base element 1 is blocked by pin 16. After inserting sleeve 8 into base 1 the sleeve is protected against sliding out by pushing rod 13 fitted with handle 14 into it. To upper support 12 is mounted the measurement arm including links 18, 19, 20, 21, 22 and movable end link 11 all connected with one another and the upper part of the support by means of revolute joints 23 and forming a serial kinematic chain. Upper support 12, links 18, 19, 20, 21, 22 and movable end link 11 are made of plastic as a single piece, while revolute joints 23 take the form of local narrowings of the material, where elastic deflections take place. To link 21 is mounted microprocessor computing system with display screen 5 and control buttons. Movable end link 11 is connected with marker 10 by means of quickly detachable connection 8, fitted with locking pin 16 and securing rod 13 with handle 14, identically to the connection of lower section of support 2 with base element 1.

Increasing the number of movable elements improves measurement accuracy. With six movable elements 18, 19, 20, 21, 22 and 11 a kinematic chain with 6 degrees of freedom is formed. The operated limb constitutes a free rigid link suspended in space, with 6 degrees of freedom of movement: 3 linear movements along axes x, y, z and 3 rotational movements around said axes, which means that the measuring arm with a system of six elements ensures the greatest accuracy of intraoperative measurements.

The invention claimed is:

1. A device for measuring femur bone displacement during a surgical procedure to correct a damaged hip, especially during a total hip arthroplasty, the device comprising:
    a base element immovably mountable to an ilium bone; and
    a measurement arm, detachably mounted to the base element via a support and fitted at least with an accelerometer located on the support and connected with a computing system unit that has a display screen and control buttons, wherein
    the measurement arm includes at least five movable links and a moveable end link, coupled serially to each other and to the support by revolute joints having one degree of freedom; and
    a three-axis accelerometer is mounted on at least every other link and connected to the computing system unit.

2. The device according to claim 1, wherein the device is fitted with a marker mountable to a femur by a screw connection.

3. The device according to claim 2, wherein the movable end link is fitted with at least one of an accelerometer, a magnetic field sensor, and a gyroscopic sensor.

4. The device according to claim 3, wherein the accelerometer, the magnetic field sensor, and the gyroscopic sensor form together an integrated sensor unit.

5. The device according to claim 4, wherein the computing system unit is mounted on the support or on one of the at least five movable links and is fitted with a display screen.

6. The device according to claim 1, wherein a movable link of the at least five movable links is fitted with an indicator of a position of characteristic points of a patient's pelvis or the patient's femur or a marker.

7. The device according to claim 1, wherein the device is fitted with a marker mountable to a femur by a screw connection and the movable end link is connected to the marker by a quickly detachable connection.

8. The device according to claim 1, wherein the device further comprises a two-piece support comprising a lower support and an upper support coupled together by a joint fitted with a motion locking mechanism.

9. The device according to claim 1, wherein the revolute joints constitute local narrowings of material where elastic deflections take place.

10. A method of making orthopedic measurements during total hip arthroplasty using a device for measuring femur bone displacement, the device having a base element immovably mountable to an ilium bone and a measurement arm detachably mounted to a base element via a support, the support comprising an upper support section and a lower support section, the measurement arm being fitted at least with an accelerometer located in the support and connected with a computing system unit, the support being coupled in series to at least five movable links and a movable end link by revolute joints having at least one degree of freedom, a three-axis accelerometer being mounted on at least every other moveable link, and the device being fitted with a computing system unit with a display screen and control buttons, the method comprising:
    determining by use of the computing system unit, based on a reading from the accelerometers located on adjacent links of the measurement arm, an angular position of the revolute joints located between the support and the at least five moveable links and the moveable end link; and
    then measuring, based on the angular positions of the revolute joints, a position of the movable end link relative to the upper support section, wherein the measurement is made at least twice, and an operating surgeon, using a display screen and buttons, controls the measurement and reads data indicating a difference between a first and a last position in directions of relevance to a patient, and wherein the operating surgeon controls the measurement such that an angle between an axis of each revolute joint and the vertical remains greater than 30°.

11. The method according to claim 10, wherein the measurement includes reading of data from the sensors over a certain period of time during which the patient and the device can be immovable or can be moved by the operating surgeon.

* * * * *